United States Patent
Norris (10) Patent No.: US 10,481,081 B2
(45) Date of Patent: Nov. 19, 2019

(54) TEXTURE ANALYSIS OF A COATED SURFACE USING PIVOT-NORMALIZATION

(71) Applicant: PPG Industries Ohio, Inc., Cleveland, OH (US)

(72) Inventor: Alison M. Norris, Avon, OH (US)

(73) Assignee: PPG Industries Ohio, Inc., Cleveland, OH (US)

( * ) Notice: Subject to any disclaimer, the term of this patent is extended or adjusted under 35 U.S.C. 154(b) by 585 days.

(21) Appl. No.: 14/535,380

(22) Filed: Nov. 7, 2014

(65) Prior Publication Data

US 2015/0134300 A1    May 14, 2015

Related U.S. Application Data (60) Provisional application No. 61/901,498, filed on Nov. 8, 2013.

(51) Int. Cl.
| | | |
|---|---|---|
| *G01N 21/25* | (2006.01) | |
| *G01N 21/55* | (2014.01) | |
| *G01J 3/46* | (2006.01) | |

(52) U.S. Cl.
CPC .............. *G01N 21/25* (2013.01); *G01J 3/463* (2013.01); *G01N 21/55* (2013.01); *G01J 2003/466* (2013.01); *G01N 2201/125* (2013.01)

(58) Field of Classification Search
None
See application file for complete search history.

(56) References Cited

U.S. PATENT DOCUMENTS

| | | | |
|---|---|---|---|
| 3,927,944 A | 12/1975 | Iwahashi | |
| 3,972,617 A | 8/1976 | Shibata | |
| 4,092,069 A | 5/1978 | Fukuda | |
| 4,164,374 A | 8/1979 | Lambe | |
| 4,344,142 A | 8/1982 | Diehr, II | |
| 4,479,718 A | 10/1984 | Alman | |
| 4,544,424 A | 10/1985 | Take | |
| 4,711,580 A | 12/1987 | Venable | |
| 5,231,472 A | 7/1993 | Marcus | |
| 5,319,437 A * | 6/1994 | Van Aken | G01J 3/02 356/326 |
| 5,590,251 A | 12/1996 | Takagi | |
| 5,612,928 A | 3/1997 | Haley | |

(Continued)

FOREIGN PATENT DOCUMENTS

| | | |
|---|---|---|
| AU | 2014346520 B2 | 5/2015 |
| CN | 1635957 A | 7/2005 |

(Continued)

OTHER PUBLICATIONS

Anonymous: "Chapter 1.3.5.17. Detection of Outliers", NIST/SEMATECH e-Handbook of Statistical Methods, Jan. 1, 2012 (Jan. 1, 2012), XP055162021.

(Continued)

*Primary Examiner* — Alexander G Ghyka
(74) *Attorney, Agent, or Firm* — Workman Nydegger (57) ABSTRACT

A method that includes obtaining, using a processor, reflectance data from a target coating and calculating, using the processor, pivot-normalized reflectance data. The method also includes generating, using the processor, a coating formulation that is the same or substantially similar in appearance to the target coating.

9 Claims, 7 Drawing Sheets

(56) References Cited

U.S. PATENT DOCUMENTS

| | | |
|---|---|---|
| 5,926,262 A | 7/1999 | Jung |
| 6,056,821 A | 5/2000 | Nihongi |
| 6,166,841 A | 12/2000 | Pringle |
| 6,249,751 B1 | 6/2001 | Asaba et al. |
| 6,449,384 B2 | 9/2002 | Di Venuto |
| 6,539,325 B1 | 3/2003 | Numata et al. |
| 6,794,669 B2 | 9/2004 | Chelvayohan et al. |
| 7,809,155 B2 | 10/2010 | Nestares |
| 7,944,561 B2 | 5/2011 | Nisper et al. |
| 8,345,252 B2 | 1/2013 | Nisper et al. |
| 8,606,731 B2 | 12/2013 | Fujieda et al. |
| 8,879,066 B2 | 11/2014 | Norris |
| 9,482,657 B2 | 11/2016 | Bell |
| 2003/0208345 A1 | 11/2003 | O'Neill |
| 2004/0218182 A1 | 11/2004 | Alman et al. |
| 2005/0128484 A1 | 6/2005 | Rodrigues |
| 2005/0169518 A1 | 8/2005 | Boston et al. |
| 2005/0206383 A1 | 9/2005 | Park |
| 2006/0030060 A1 | 2/2006 | Noguchi et al. |
| 2006/0045831 A1 | 3/2006 | Galembeck |
| 2006/0245632 A1 | 11/2006 | Nisper et al. |
| 2007/0019887 A1 | 1/2007 | Nestares |
| 2007/0172113 A1 | 7/2007 | Sai et al. |
| 2007/0200337 A1 | 8/2007 | Johnson et al. |
| 2007/0226158 A1 | 9/2007 | Woronow |
| 2007/0250273 A1 | 10/2007 | De Haas |
| 2008/0177586 A1 | 7/2008 | Jamjoom |
| 2008/0235224 A1 | 9/2008 | Rodrigues et al. |
| 2008/0278723 A1 | 11/2008 | Merchak |
| 2009/0015835 A1 | 1/2009 | Balakrishnen et al. |
| 2009/0157212 A1 | 6/2009 | McClanahan |
| 2009/0190839 A1 | 7/2009 | Higgins |
| 2009/0213120 A1* | 8/2009 | Nisper .............. G01J 3/504 345/426 |
| 2009/0292520 A1* | 11/2009 | Nwankpa ............ G06F 17/16 703/18 |
| 2010/0048242 A1 | 2/2010 | Rhoads |
| 2010/0228511 A1 | 9/2010 | Chin et al. |
| 2011/0242562 A1* | 10/2011 | Vrhel .............. H04N 1/60 358/1.9 |
| 2011/0250351 A1* | 10/2011 | Steenhoek .......... B32B 43/00 427/140 |
| 2011/0282613 A1 | 11/2011 | Skinner |
| 2012/0225190 A1* | 9/2012 | Steenhoek .......... G01N 21/25 427/8 |
| 2012/0243797 A1 | 9/2012 | Di Venuto |
| 2012/0253749 A1* | 10/2012 | Bernard ............ G01N 21/55 702/189 |
| 2012/0303376 A1* | 11/2012 | Shishido ........... G06Q 30/02 705/1.1 |
| 2013/0069970 A1* | 3/2013 | Sasaki ............. G06T 15/06 345/589 |
| 2013/0244197 A1 | 9/2013 | Tijoe |
| 2014/0078293 A1 | 3/2014 | Beymore |
| 2014/0118936 A1 | 5/2014 | Merlet et al. |
| 2014/0242271 A1 | 8/2014 | Prakash et al. |
| 2014/0250109 A1 | 9/2014 | Wang |
| 2014/0278251 A1 | 9/2014 | Norris |
| 2014/0278253 A1 | 9/2014 | Beymore |
| 2014/0278254 A1 | 9/2014 | Beymore |
| 2015/0023054 A1 | 1/2015 | Goda et al. |
| 2015/0127269 A1 | 5/2015 | Bell |
| 2015/0134269 A1 | 5/2015 | Norris |
| 2015/0134299 A1 | 5/2015 | Norris |
| 2015/0134300 A1 | 5/2015 | Norris |

FOREIGN PATENT DOCUMENTS

| | | |
|---|---|---|
| CN | 1797420 | 7/2006 |
| CN | 101184986 | 5/2008 |
| CN | 101646929 | 2/2010 |
| CN | 101784871 | 7/2010 |
| CN | 102549545 | 7/2012 |
| JP | 07150081 | 6/1995 |
| JP | 2002236850 | 8/2002 |
| JP | 6-23968 A | 1/2006 |
| JP | 2006277555 | 10/2006 |
| JP | 2007218895 | 8/2007 |
| JP | 2008-190880 | 8/2008 |
| JP | 2009-75751 | 4/2009 |
| JP | 2009-204622 A | 9/2009 |
| JP | 2008-141682 | 12/2009 |
| JP | 2010242018 | 10/2010 |
| JP | 6290406 B2 | 3/2018 |
| KR | 2002-0070360 | 9/2002 |
| KR | 20100102147 | 9/2010 |
| TW | 200608310 | 3/2006 |
| TW | 200821602 | 5/2008 |
| TW | 200834273 | 8/2008 |
| TW | 201339652 A | 10/2013 |
| WO | 03063719 A1 | 8/2003 |
| WO | 2006096521 | 9/2006 |
| WO | 2006112864 | 10/2006 |
| WO | 2007096402 | 1/2009 |
| WO | WO 2013049792 A1 | 4/2013 |
| WO | 2013116192 | 8/2013 |
| WO | 2014150337 | 9/2014 |

OTHER PUBLICATIONS

URL:http://www.itl.nist.gov/div898/handbook/eds/section 3/eda36h.htm [retrieved on Jan. 14, 2015] the whole document.

Paravina R D et al; "Evaluation of blending effect of composites related to restoration size", Dental Materials, Elsevier, Amsterdam, NL, vol. 22, No. 4, Apr. 1, 2006 (Apr. 1, 2006) pp. 299-307, XP027943381, ISSN: 0109-5641 [retrieved on Apr. 1, 2006], table 2.

Takagi et al, "Prediction of spectral reflectance factor distribution of color-shift paint finishes", Color Research & Application, John Wiley & Sons, Inc., US, vol. 32, No. 5, Oct. 1, 2007, pp. 378-387, XP002604927, ISSN: 0361-2317.

Beymore, Paul M., U.S. Appl. No. 14/121,869, "Pigment Identification of Complex Coating Mixtures with Sparkle Color", filed Oct. 28, 2014.

Office Action in application No. 201480070100.X dated Feb. 27, 2017.

Non-Final Office Action for U.S. Appl. No. 14/535,399 dated Apr. 4, 2017.

Final Office Action for U.S. Appl. No. 14/535,399 dated Nov. 1, 2017.

Final Office Action for U.S. Appl. No. 14/535,372 dated Oct. 6, 2017.

Non-Final Office Action for U.S. Appl. No. 14/535,372 dated Jun. 20, 2017.

Non-Final Office Action for U.S. Appl. No. 13/832,116 dated Mar. 5, 2014.

Kuncheva, Ludmila I., James C. Bezdek, and Robert PW Duin. "Decision templates for multiple classifier fusion: an experimental comparison." "Patternrecognition 34.2.2001."

Korean Office Action in application No. 201507025129 dated Jun. 21, 2016.

Final Office Action for U.S. Appl. No. 13/832,554 dated Apr. 20, 2016.

I. Lissner, U. Philipp: "Upgrading Color-Difference Formulas", Journal of the Optical Society of America, vol. 27 No. 7, Jun. 11, 2010 (Jun. 11, 2010), pp. 1620-1629, XP055152562, DOI: 10,1364/JOSAA.27.001620 Sections 1 and 2.A.

D. Puig, M.A. Garcia, J. Melendez: "Application-Independent feature selection for texture classification", Pattern Recognition, vol. 43, No. 10, May 10, 2010 (May 10, 2010) pp. 3182-3297, XP027095420, DOI: 10. 1016/j.patcog.2010.05.005 abstract and section 3.

J.H. Xin, S. Shao, K.F.-L. Chung: "Colour-appearance modelling using feedforward networks with Bayesian regularization method-part 1: forward model", Color Research & Application, vol. 25, No. 6, Oct. 13, 2000, pp. 424-434, XP055152560, DOI: 10.1002/1520-6378(200012)25:6<424:AID-COL7>3.0.CO;2-Q.

(56) References Cited

OTHER PUBLICATIONS

E. Kirchner: "Appearance and measurement modeling an drendering of the visual texture of automotive paints", Detroit Color Council, Mar. 13, 2013, XP055153196, Retreived from the Internet: URL: http://www.detroitcc.org/files/2013March14b.pdf, [retireved on Apr. 4, 2013] Models for predicting Texture.
E.J.J. Kirchner, J. Ravi: "Setting tolerances on color and texture for automotive coatings", Color Research & Application, vol. 39, No. 1, Jul. 25, 2012 pp. 88-98, XP055152561, DOI:10.1002/col.21767.
PPG Automotive Refinish: "RapidMatch™ X-5:guida utente", Pittsburgh Plate Glass (PPG) Industries, 2013, XP055153237, retrieved from the Internet: URL:http://it.nexaautocolor.com/media/213903/rapidmatch_v1-2012_email_version.pdf [retrieved on Sep. 22, 2014].
Non-Final Office Action for U.S. Appl. No. 13/832,554 dated Sep. 23, 2015.
Kokla, Vassiliki et al., A Bayesian decision model for watercolour analysis, Proc. of SPIE, 2007, vol. 6618, pp. 66180S-1-66180S-9.
Korean Office Action for application No. 2015/7025129 dated Dec. 29, 2016.
Chinese Office Action for application No. 201480015524.6 dated Dec. 26, 2016.
Final Office Action for U.S. Appl. No. 13/832,554 dated Sep. 6, 2017.
Non-Final Office Action for U.S. Appl. No. 13/832,554 dated May 2, 2017.
Alice vs CLS Bank (Supreme Court Decision) (2013).
Notice of Allowance from U.S. Appl. No. 13/835,675 dated Nov. 1, 2016.
Non-Final Office Action from U.S. Appl. No. 13/835,675 dated Sep. 16, 2015.
Taiwan Office Action for application No. 103109480 dated Sep. 17, 2015.
Taiwan Office Action for application No. 103109480 completed on Jul. 17, 2016.
Korean Office Action in application No. 2015-7025121 dated Jul. 25, 2016.
International Search Report for application No. PCT/US2014/022983 dated Nov. 28, 2014.
Korean Office Action in application No. 2015-7025121 dated Jan. 31, 2017.
Chinese Office Action in application No. 201480015523.1 dated Feb. 7, 2017.
Non-Final Office Action in U.S. Appl. No. 13/835,675 dated May 2, 2017.
Final Office Action for U.S. Appl. No. 13/835,675 dated Dec. 12, 2017.
Non-Final Office Action for U.S. Appl. No. 13/832,554 dated Dec. 12, 2017.
Wang Qiang, "Texture Analysis and Classification Based on Bayesian Network Model", Computer Aided Design & Computer Graphics, Dec. 31, 2007, pp. 1565-1568.
Takuro Yonezawa, "An Event Decription Language Using Temporal Relation for Smart Object Services", IPSJ SIG Technical Report 2008-MBL-44, Mobile computing and ubiquitous communication, 2008-UBI-17, Ubiquitous computing system, Information Processing Society of Japan, Feb. 27, 2008, vol. 2008, No. 18, pp. 75-82.
Japanese Office Action for application No. JP 2016-501119 dated Nov. 7, 2016.
Non-Final Office Action for U.S. Appl. No. 14/535,372 dated Apr. 26, 2018.
Non-Final Office Action for U.S. Appl. No. 14/535,372 dated Feb. 15, 2018.
Li Sun and Richard M. Crooks in Molecular Interactions between Organized, Surface Confided Monolayers and Vapor-Phase Probe Molecules. 5. Acid-Base Interactions, 1993 American Chemical Society, pp. 1775-1780.
Final Office Action for U.S. Appl. No. 13/832,554 dated Mar. 26, 2018.
Massonnet et al., "Identification of organiz pigments in coatings: applications to red automotive topcoats", First Neeting of the European Academy of Forensic Sciences, 1997.
Harkins et al., Identification of pigments in paint products by infrared spectroscopy, Analystical Chemistry, 1959.
Janina et al., "Examination of multilayer paint coats by the use of infrared, Raman and XRF spectroscopy for forensic purposes", J. of Molecular Structure, 2006.
Rafik, "Bulk optical properties of phthalocyanine pigment particles", Can J. Chem, 1980.
Office Action dated Mar. 6, 2017 from Canadian Patent Application No. 2930019 published Aug. 1, 2007.
Office Action dated Mar. 12, 2018 from Canadian Patent Application No. 2930019 published Aug. 1, 2007.
Office Action dated Dec. 27, 2018 from Canadian Patent Application No. 2930019 published Aug. 1, 2007.
International Search Report dated Jan. 27, 2015 from International Patent Application Na PCT/US2014/064766 filed Nov. 10, 2014.
International Preliminary Report on Patentability dated May 10, 2016 from International Patent Application No. PCT/US2014/064766 filed Nov. 10, 2014.
Office Action dated May 16, 2017 from Japanese Patent Application No. 2016528108 filed May 6, 2016.
Decision to Grant dated Jan. 23, 2018 from Japanese Patent Application No. 2016528108 filed May 6, 2016.
Notification of Patent Grant dated Nov. 14, 2017 from Chinese Patent Application No. 201480070100.X filed Jun. 20, 2016.
Office Action dated Jun. 13, 2018 from Korean Patent Application No. 2016-7015255 filed Jun. 8, 2016.
Office Action dated Oct. 17, 2018 from Indian Patent Application No. 201617016019 filed May 7, 2016.
Office Action dated Jun. 26, 2018 from Mexican Patent Application No. 16/006021 filed May 9, 2016.
Notice of Allowance dated Jul. 8, 2014 from U.S. Appl. No. 13/832,116, filed Mar. 15, 2013.
Office action dated Oct. 30, 2018 from U.S. Appl. No. 13/832,554, filed Mar. 15, 2013.
Office Action dated Feb. 4, 2016 from U.S. Appl. No. 13/835,675, filed Mar. 15, 2013.
Advisory Action dated Jul. 3, 2016 from U.S. Appl. No. 13/835,675, filed Mar. 15, 2013.
Notice of Allowance dated Apr. 13, 2018 from U.S. Appl. No. 13/835,675, filed Mar. 15, 2013.
Notice of Allowance dated Aug. 7, 2018 from U.S. Appl. No. 13/835,675, filed Mar. 15, 2013.
International Preliminary Report on Patentability dated Sep. 15, 2015 from International Patent Application No. PCT/US2014/022983 filed Mar. 11, 2014.
Office Action dated Jun. 21, 2016 from Korean Patent Application No. 2015-7025121 filed Mar. 11, 2014.
Office Action dated Jan. 11, 2017 from Chinese Patent Application No. 2014800155211 filed Mar. 11, 2014.
Office Action dated Aug. 11, 2017 from Chinese Patent Application No. 2014800155211 filed Mar. 11, 2014.
Decision to Grant dated Nov. 16, 2018 from Korean Patent Application No. 2016-7015255 filed Jun. 8, 2016.
Decision to Grant dated May 12, 2017 from Japanese Patent Application No. 2016-501119 filed Aug. 31, 2015.

\* cited by examiner

TEXTURE ANALYSIS OF A COATED SURFACE USING PIVOT-NORMALIZATION

CROSS REFERENCE TO RELATED APPLICATION

The present application claims priority to U.S. Provisional Application No. 61/901,498, filed on Nov. 8, 2013.

FIELD OF THE INVENTION

In various embodiments, the present invention generally relates to a method and apparatus that use a pivot-normalization to relate spectral reflectances or colorimetric information from spectrophotometric angles and/or incident light sources to identify the proper pigment(s) to match both the texture and/or gonioapparent effect(s) occurring within an unknown target coating.

BACKGROUND OF THE INVENTION

In a standard portable spectrophotometer, the incident light is generally, set at an angle of forty-five (45) degrees from normal. The resulting spectral reflectances that can be gathered are generally in the same plane as the incident light and are on either side of the specular angle (equal and opposite angle to the incident light) as well as nearer to the incident light source itself.

New portable spectrophotometric devices offer a vast multitude of angular color response (spectral reflectance) data. Besides the addition of several new angles, including azimuthal, or out-of-plane, angles, many instruments also offer additional light sources with different geometries from standard. By way of example, the incident light source of a second illuminator may be located at fifteen (15) degrees from normal. The plurality of combinations of incident light and angular response can be both too little and too much information to be handled at one time.

Thus, a need exists for systems and methods that may be used to evaluate all of the data and specific combinations of data from a spectrophotometer. There is also a need for systems and methods in which the individual angular spectral reflectance and colorimetric (e.g. XYZ, L*a*b*, L*C*h*, etc.) responses are handled as both independent entities as well as entities dependent upon the other responses (whether all responses or specifically selected responses) received from the device.

SUMMARY OF THE INVENTION

In a first aspect, embodiments of the invention provide a computer implemented method. The method includes obtaining, using a processor, reflectance data from a target coating and calculating, using the processor, pivot-normalized reflectance data. The method also includes generating, using the processor, a coating formulation that is the same or substantially similar in appearance to the target coating.

In another aspect, embodiments of the invention are directed to a system. The system includes a database and a processor in communication with the database. The processor is programmed to obtain reflectance data from a target coating, calculate pivot-normalized reflectance data, and generate a coating formulation that is the same or substantially similar in appearance to the target coating.

In another aspect, embodiments of the invention provide an apparatus. The apparatus includes means for obtaining reflectance data from a target coating and means for calculating pivot-normalized reflectance data. The apparatus also includes means for generating a coating formulation that is the same or substantially similar in appearance to the target coating.

In a further aspect, embodiments of the invention provide a non-transitory computer readable medium including software for causing a processor to: obtain reflectance data from a target coating; calculate pivot-normalized reflectance data; and generate a coating formulation that is the same or substantially similar in appearance to the target coating.

DETAILED DESCRIPTION OF THE INVENTION

While the description herein generally refers to paint, it should be understood that the devices, systems and methods apply to other types of coatings, including stain and industrial coatings. The described embodiments of the invention should not be considered as limiting. A method consistent with the present invention may be practiced in a variety of fields such as the matching and/or coordination of apparel and fashion products.

Embodiments of the invention may be used with or incorporated in a computer system that may be a standalone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

Embodiments of the invention are directed generally to spectral analysis of coatings, and more particularly, but not by way of limitation, to devices, methods and systems for predicting and formulating a complex coating mixture containing metallic, pearlescent, and/or special effect pigments.

In various embodiments, the present invention generally relates to a method and apparatus for identifying physical property attributes of cured complex coating (e.g., paint) mixtures using pivot-normalization data that are calculated, using a processor, based on the spectral reflectance and colorimetric response from a spectrophotometer.

In various embodiments, the purpose of using pivot-normalization methodology is multi-fold. First, in order to use all available angles within a given system, pivot-normalization may be used to create an alternate bi-directional reflectance distribution function ("BRDF")-type analysis. This type of analysis does not exclude any angles, but uses all angles to create a hemispherical "map" or "fingerprint" of a particular texture or pigment type, whether gonioapparent or not. Second, pivot-normalization may be used to evaluate only specific combinations of angles in order to achieve purposeful manipulations. Similarly, this includes the specific exclusion or inclusion of specific singular angles or combinations of angles when a particular texture or effect is being sought after as included or not included in a target coating. Third, pivot-normalization may be used to accommodate for and correct the potential assumption that the received spectral reflectance values are incorrect in some way. Some potential reasons for irregularity or abnormality of the spectral reflectance data, even if minor, may include incident light angle location, incident light fluctuation, aperture size, target coating surface non-uniformity, etc.

Figure 1:
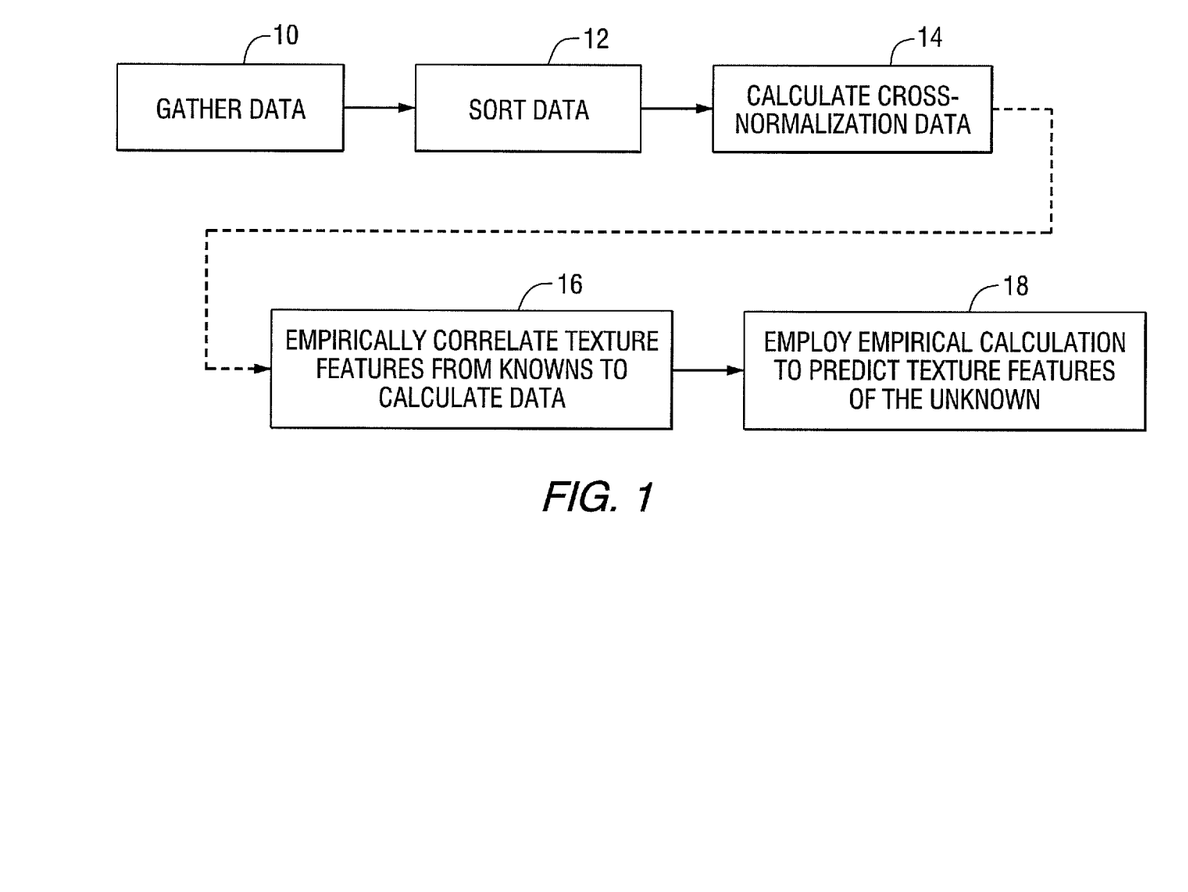
FIG. 1 illustrates an embodiment of a process that calculates a formula for a target complex coating.

FIG. 1 illustrates an embodiment of a process that calculates a formula for a target complex coating. At step 10, data is gathered from, for example, a spectrophotometer. In various embodiments, the systems and methods of the present invention may be employed in several ways. For example, the systems and methods may be used on raw data, for example spectral reflectance data and/or colorimetric (e.g., XYZ, L*a*b*, L*C*h*, etc.) and data that may have already been treated. The data are treated data that may include, but are not limited to, multi-dimensional geometric data, vector data, unmodified or modified specular spectral reflectance data, etc. In various embodiments, the data that undergoes pivot-normalization may have two or more identified, associated arrays based on the functionality of the original data. For example, spectral reflectance data may be considered to have arrays comprised of angle and wavelength. Another example includes colorimetric data as a function of angle and reference type (i.e., L*, a*, or b*). In situations where more than two arrays exist, various sets of two may be tested independently, or the various arrays may be condensed into only two arrays. In various embodiments, in order to choose the optimal set of arrays within a data set, testing may be required on several scenarios to both the variety of potential resulting pivot-normalized data sets and the optimum based on desired functionality of the algorithm, with respect to color, texture, pigmentation and all variations within complex mixtures.

Figure 2:
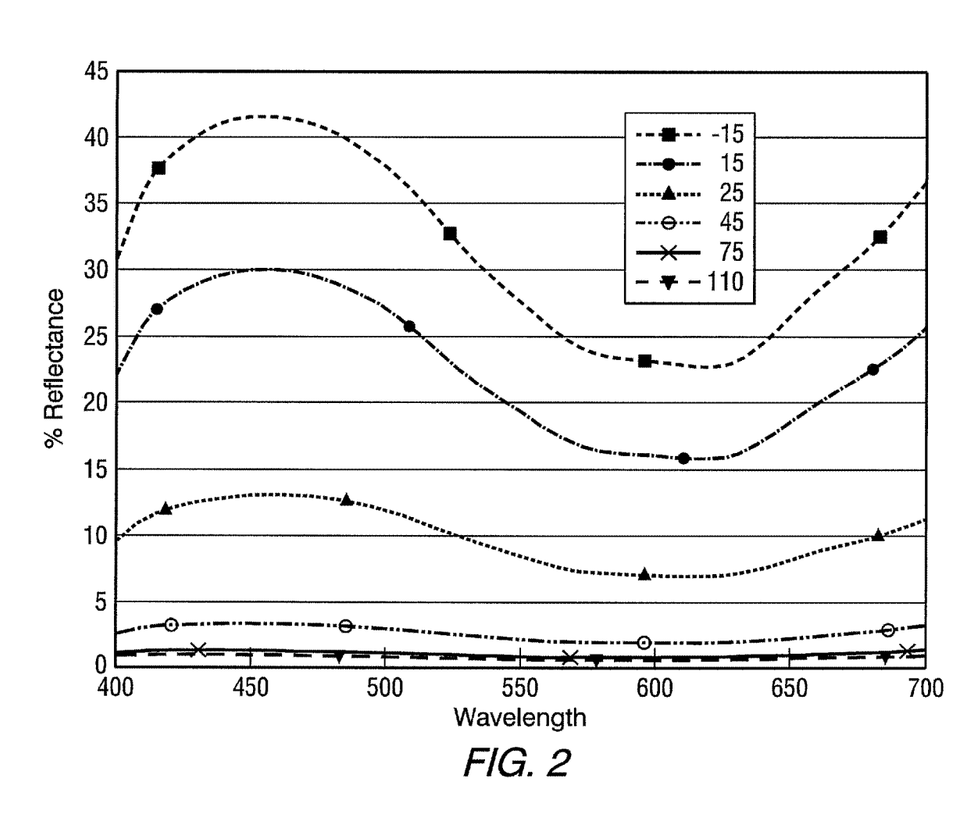
FIG. 2 illustrates an example of raw spectral reflectance data from an industry-standard six angles.
Figure 3:
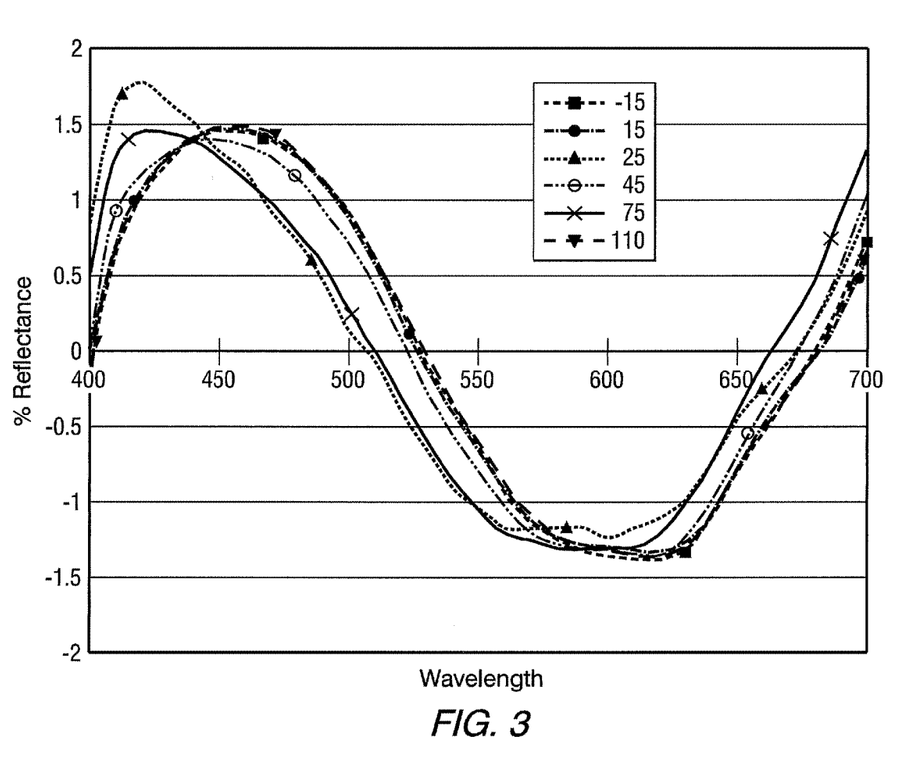
FIG. 3 illustrates an example of a "standard" normalization result.
Figure 4:
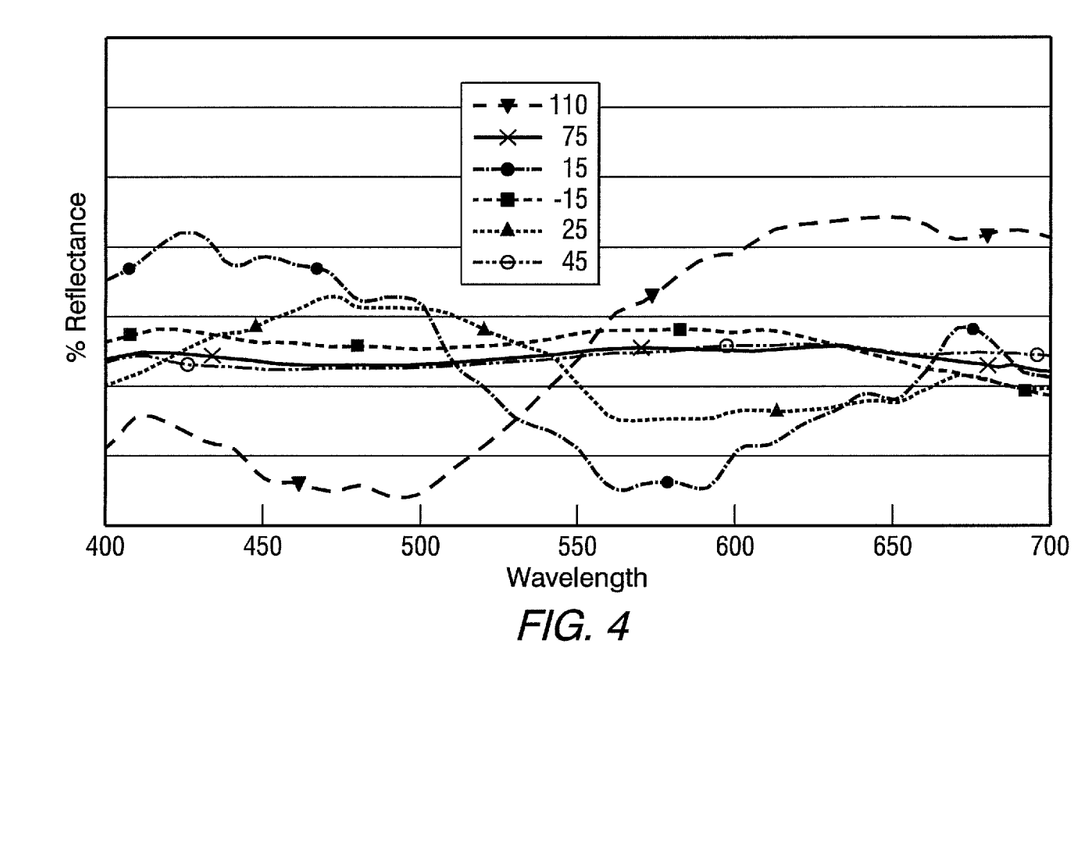
FIG. 4 illustrates an example of various pivot-normalized curves overlaying each other.

FIG. 2 illustrates an example of raw spectral reflectance data from an industry-standard six angles. In a "standard" normalization situation, the goal of the process is to adjust differing scales of data from multiple data sets (i.e. different angles) to one common scale, thus creating a set of shifted or scaled data that allow for relational analysis and understanding between the original data sets. An example of a "standard" normalization result is illustrated in FIG. 3. In various embodiments, the goal of the pivot-normalization of the present invention is not to align differing scales to a common scale, but to cause further separation in order to gain improved insight as to similarities and differences between the original data sets and their associated arrays of information. FIG. 4 illustrates an example of various pivot-normalized curves overlaying each other. As can be seen, there is a difference between the resultant information from a "standard" normalization method versus a pivot-normalized method. In FIG. 4 the resolution of the graph has been accounted for using an overlay method rather than aligning the y-axes of each curve.

At step 12 of FIG. 1, the data are sorted based on a secondary array of associated information. For example, if using raw spectral reflectance data with associated arrays of angle and wavelength, the data may be sorted by wavelength in order to create a commonality between the scales of the angles within the individual wavelengths. This is contrary to a "standard" normalization method, which sorts by angle in to make a common alignment between the scales of the wavelengths within individual angles. In various embodiments, by sorting by the secondary array first (e.g., the wavelength), the angles become the "commonality." Within each set of the secondary array, the pivot-normalization calculation at step 14 may take on a standard form. In various embodiments, the normalization calculation is:

$$\frac{X - \mu}{\sigma} \qquad \text{Equation (1)}$$

where X is the specific data set value, $\mu$ is the sample or population average of the data set values within the sorted secondary array, and $\sigma$ is the sample or population standard deviation of the data set values within the sorted secondary array.

Due to the fact that the standard deviation across the first array of data may be much smaller than that across the second array of data, the resultant pivot-normalized set of data may appear to not yield useful information. Thus, if the resolution of the inspection, analysis, graphing, etc. is poor, detailed features may be missed. Therefore, the resolution of the inspection, analysis, graphing, etc. may be optimized so as to ascertain the benefits of the analysis.

In various embodiments, when using spectral reflectance data, the calculation may occur individually for the first array of data based on each secondary array of data. However, the output remains linked with the original two associated arrays. Statistics, such as for example mean, median, and sum may be used to create a singular array out of multi-array calculated pivot-normalized data. In another embodiment, an individual specific array value or values may be compared between the pivot-normalized analyses. The value of such a situation is to focus on the particular array value or values of maximum or statistical significance, where a majority of color and/or texture information is visibly or numerically perceived.

At step 16 of FIG. 1, the calculated pivot-normalized values or statistics from the pivot-normalized data may further be empirically correlated to known characteristics in order to identify textures, primary flake types, or other appearance information in complex coating mixtures. To employ an empirical method, the pivot-normalized data is calculated for an empirical dataset. All desired statistical or mathematical conversions of the data into a single point may be employed, or the data may remain as functions of the first and second arrays of linked information. In various embodiments, the empirical data set is representative of the expected mixtures and colors that will need to be handled in everyday situations. The empirical data set may be used to create a predictive correlation: y=f(x), where y represents the desired characteristic for identification or a qualitative question regarding the target coating, and f(x) is some function of x's, where x is one or multiple variables using the pivot-normalized calculated values or statistics from the pivot-normalized data from a specific set or multiple sets of associated arrays. The resulting function may be linear or non-linear as defined by the empirical data set.

Figure 5:
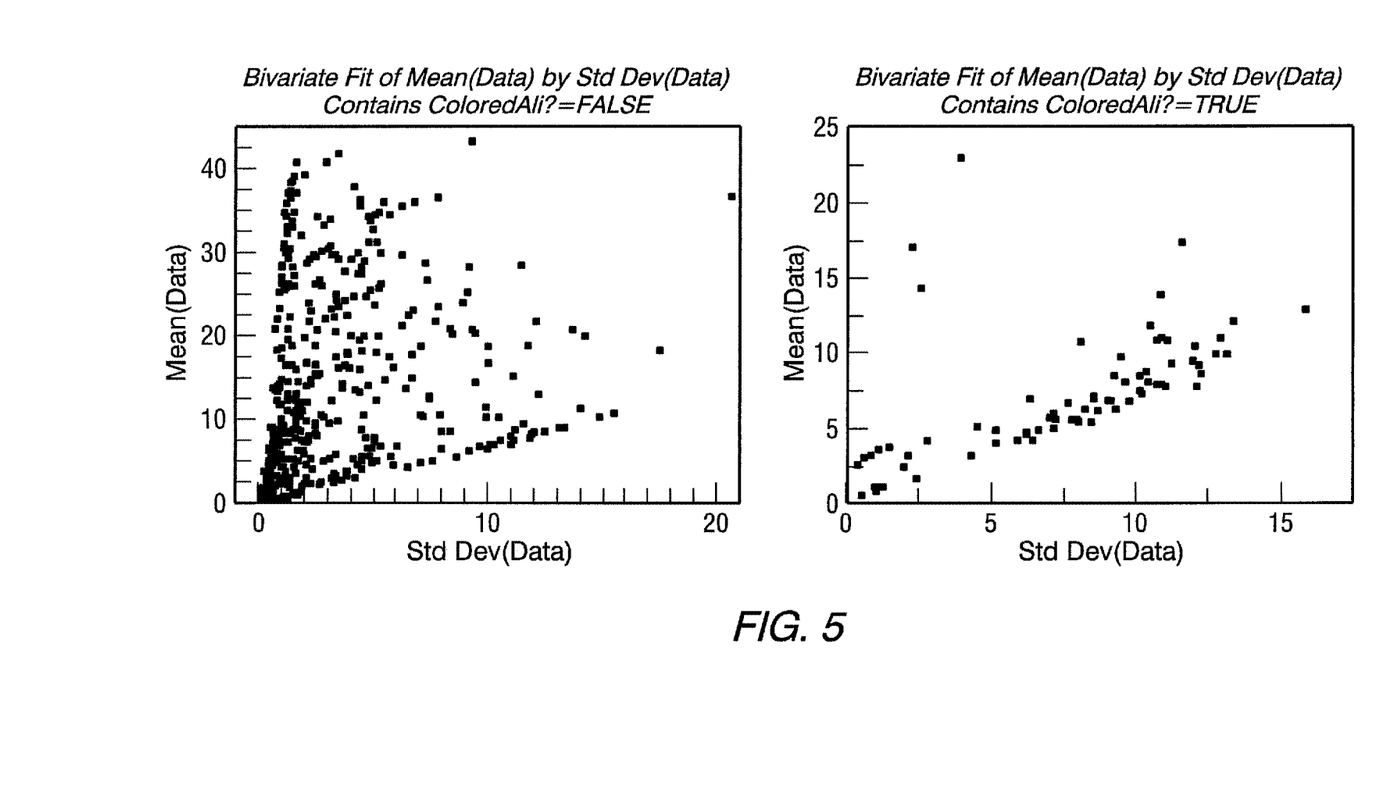
FIG. 5 illustrates an example of the use of pivot-normalized reflectance data where the mean and standard deviation have been calculated across the first array of associated information and graphed against one another.

FIG. 5 illustrates an example of the use of pivot-normalized reflectance data where the mean and standard deviation have been calculated across the first array of associated information and graphed against one another. The resulting correlations show a high probability of the usage of a colored aluminum pigment only in specific situations, whereas the lack of usage of a colored aluminum pigment exemplifies a significantly different graphical display and therefore also associated probabilities.

Figure 6:
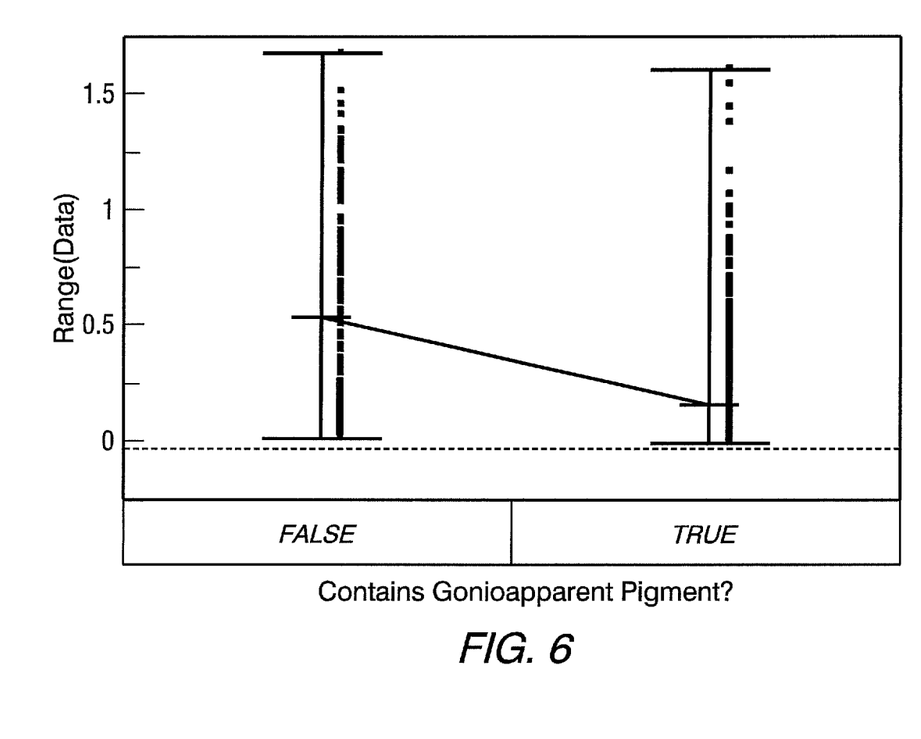
FIG. 6 illustrates an example of the use of a pivot-normalized data set using a specific set of angles to predict whether a target coating will contain a gonioapparent effect.

FIG. 6 illustrates an example of the use of a pivot-normalized data set using a specific set of angles to predict whether a target coating will contain a gonioapparent effect. In this case, a calculated range value from the pivot-normalized data for the particular angles resulting in 0.5 or above indicates a higher likelihood of not containing a gonioapparent pigment, whereas a calculated range value closer to 0.2 or below has a higher likelihood of containing the gonioapparent pigment in question.

Once an empirical correlation has been determined, it may be used at step 18 of FIG. 1 to derive the predicted value for the target coating. This may be achieved by using the target coating's values for the x's (pivot-normalized data, etc.) and calculating the answer for y (the texture effect). While examples have been given herein for the content of a gonioapparent pigment, embodiments of the present invention may derive a result as specific as which gonioapparent pigment at which size flake of that pigment by iteratively choosing the most important single angles or combinations of angles for the pivot-normalization calculations and empirical correlations. The choice of angular comparisons and to what level they are combined may be used to create the best possible empirical correlation. In various embodiments, empirical correlations may also be improved by including other non-pivot-normalization information, for example singular angle colorimetric data.

In various embodiments, the quality of the overall "map," or "fingerprint," approach and the quality of the empirical correlation approach may be dependent upon the quality of the input data. The quality of the input data may be dependent upon the quality of the instrumentation and the quality of the data set used to create a set of known data for the overall map or the empirical correlation. While any quality of data from an instrument or an empirical data set will result in an answer, the answer may be improved with the use of a high quality instrument and a widely varied, high quality empirical data set.

The entire set of calculations described herein may be used in conjunction with a processor in order to facilitate the choice of specific associated array combinations as well as accommodate the volume of calculations required in order to derive and then use an empirical correlation using pivot-normalized data.

Figure 7:
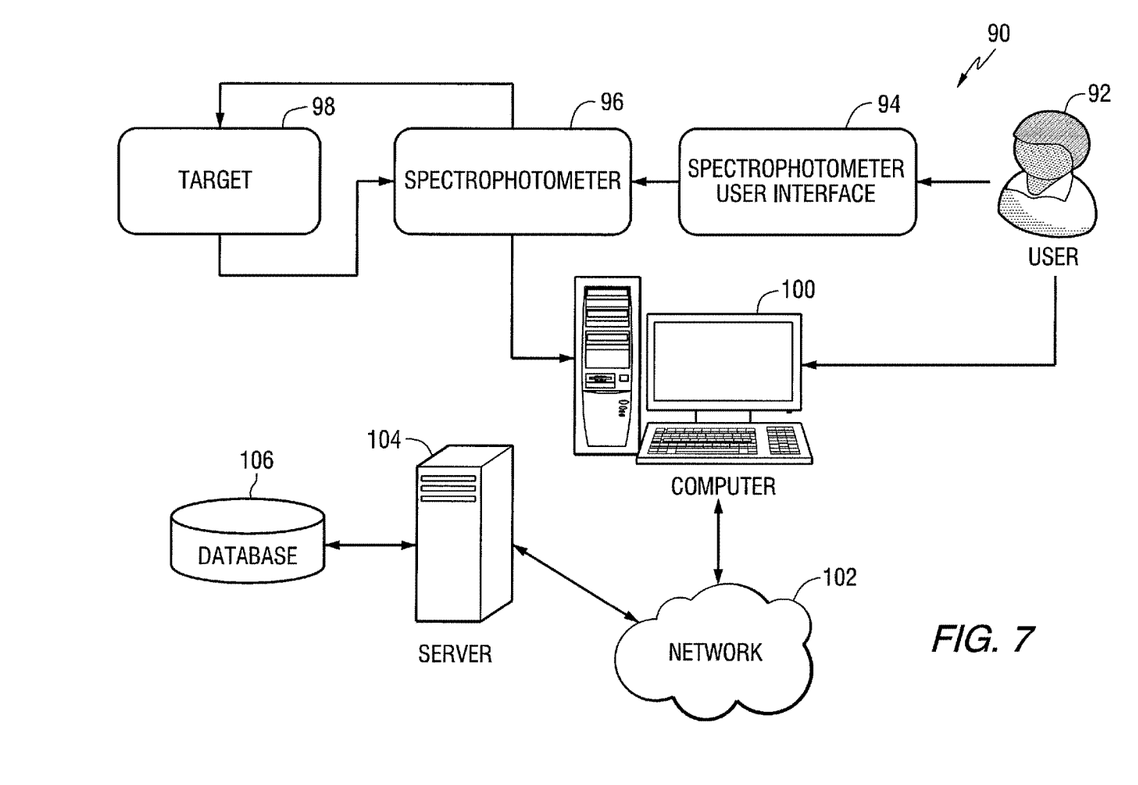
FIG. 7 illustrates an embodiment of a system which may be used to identify physical property attributes of a coating mixture of a target sample.

FIG. 7 illustrates an embodiment of a system 90 which may be used to identify physical property, attributes of a coating mixture of a target sample. A user 92 may utilize a user interface 94, such as a graphical user interface, to operate a spectrophotometer 96 to measure the properties of a target sample 98. The data from the spectrophotometer 96 may be transferred to a computer 100, such as a personal computer, a mobile device, or any type of processor. The computer 100 may be in communication, via a network 102, with a server 104. The network 102 may be any type of network, such as the Internet, a local area network, an intranet, or a wireless network. The server 104 is in communication with a database 106 that may store the data and information that is used by the methods of embodiments of the present invention for comparison purposes. In various embodiments the database 106 may be utilized in, for example, a client server environment or in, for example, a web based environment such as a cloud computing environment. Various steps of the methods of embodiments of the present invention may be performed by the computer 100 and/or the server 104.

It will be readily appreciated by those skilled in the art that modifications may be made to the invention without departing from the concepts disclosed in the forgoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

In another aspect, the invention may be implemented as a non-transitory computer readable medium containing software for causing a computer or computer system to perform the method described above. The software can include various modules that are used to enable a processor and a user interface to perform the methods described herein.

It will be readily appreciated by those skilled in the art that modifications may be made to the invention without departing from the concepts disclosed in the forgoing description. Accordingly, the particular embodiments described in detail herein are illustrative only and are not limiting to the scope of the invention.

What is claimed is:

1. A computer implemented method for efficiently analyzing multi-angle reflectance data taken from a multi-angle spectrophotometer and generating a matched coating, comprising:

obtaining, using a processor, reflectance data from a target coating, wherein the obtained data comprise color responses taken from multiple angles, and the obtained data comprise two or more associated arrays including a primary array of angle data, and a secondary array of at least wavelength data;

sorting, via the processor, the obtained data by the wavelength data in the secondary array;

calculating, using the processor, pivot-normalized reflectance data according to:

$$\frac{X - \mu}{\sigma} \qquad \text{Equation (1)}$$

wherein:
X is a specific data set value, $\mu$ is a sample or population average of the data set values within the secondary array, and $\sigma$ is a sample or population standard deviation of the data set values within the sorted secondary array;

generating a normalized, wavelength sorted hemispherical map based upon the angle data associated with the reflectance data; and based upon the normalized, wavelength sorted hemispherical map, generating, using the processor, a coating formulation that is the same in appearance to the target coating;

wherein generating the coating formulation comprises:
empirically correlating the wavelength-sorted reflectance data for the target coating to reflectance data sorted by wavelength for an empirical dataset; and predicting at least one texture feature of the target coating based on the correlation in reflectance data among wavelength-sorted data sets.

2. The method of claim 1, wherein predicting at least one texture feature comprises determining from the empirical correlation that a gonioapparent pigment is present.

3. The method of claim 2, further comprising determining from the empirical correlation which particular gonioapparent pigment is present at a particular flake size.

4. The method of claim 2, further comprising:
determining that a first texture feature is associated with one or more first angles of reflectance data taken from the spectrophotometer.

5. A system comprising a computer system, a processor, and a spectrophotometer in communication over a network, the system for efficiently analyzing multi-angle reflectance data taken from a multi-angle spectrophotometer and generating a matched coating, comprising:
a database; and
a processor in communication with the database and programmed to:
obtain reflectance data from a target coating, wherein the obtained data comprise color responses taken from multiple angles, and the obtained data comprise two or more associated arrays including a primary array of angle data, and a secondary array of colorimetric data;
sort, via the processor, the obtained data by the colorimetric data in the secondary array;
calculate pivot-normalized reflectance data, according to:

$$\frac{X - \mu}{\sigma} \quad \text{Equation (1)}$$

wherein:
X is a specific data set value, µ is a sample or population average of the data set values within the secondary array, and a is a sample or population standard deviation of the data set values within the sorted secondary array;
generate a normalized, wavelength sorted hemispherical map based upon the angle data associated with the reflectance data; and
based upon the normalized, wavelength sorted hemispherical map, generate a coating formulation that is the same in appearance to the target coating;
wherein generating the coating formulation comprises:
empirically correlating the colorimetric-sorted reflectance data for the target coating to reflectance data sorted by colorimetric data for an empirical dataset; and
predicting at least one texture feature of the target coating based on the correlation in reflectance data among wavelength-sorted data sets.

6. The system of claim 5, wherein the system is further programmed to:
determine from the empirical correlation that a gonioapparent pigment is present.

7. The system of claim 5, wherein the system is further programmed to:
determine from the empirical correlation which particular gonioapparent pigment is present at a particular flake size.

8. The system of claim 5, wherein the system is further programmed to:
determine from the empirical correlation which particular gonioapparent pigment is present at a particular flake size; and
determine that a first texture feature is associated with one or more first angles of reflectance data taken from the spectrophotometer.

9. A non-transitory computer readable medium including software comprising computer-executable instructions that, when executed, cause a processor to:
obtain reflectance data from a target coating, wherein the obtained data comprise color responses taken from multiple angles, and the obtained data comprise two or more associated arrays including a primary array of angle data, and a secondary array of wavelength data or colorimetric data;
sort, via the processor, the obtained data by the wavelength data or colorimetric data of the secondary array;
calculate pivot-normalized reflectance data, according to:

$$\frac{X - \mu}{\sigma} \quad \text{Equation (1)}$$

wherein:
X is a specific data set value, µ is a sample or population average of the data set values within the secondary array, and a is a sample or population standard deviation of the data set values within the sorted secondary array;
generate a normalized, wavelength sorted hemispherical map based upon the angle data associated with the reflectance data; and
based upon the normalized, wavelength sorted hemispherical map, generate a coating formulation that is the same in appearance to the target coating;
wherein generating the coating formulation comprises:
empirically correlating the wavelength- or colorimetric-sorted reflectance data for the target coating to wavelength- or colorimetric-sorted reflectance data calculated for an empirical dataset; and
predicting at least one texture feature of the target coating based on the correlation in reflectance data.

* * * * *